United States Patent
Kaufman et al.

(10) Patent No.: US 11,311,456 B2
(45) Date of Patent: Apr. 26, 2022

(54) ASSISTING A CPR TREATMENT

(71) Applicant: ZOLL Medical Corporation, Chelmsford, MA (US)

(72) Inventors: Christopher Luke Kaufman, Somerville, MA (US); Gary A. Freeman, Waltham, MA (US); Ulrich Herken, Medford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 1207 days.

(21) Appl. No.: 15/179,898

(22) Filed: Jun. 10, 2016

(65) Prior Publication Data

US 2017/0000688 A1 Jan. 5, 2017

Related U.S. Application Data

(60) Provisional application No. 62/175,086, filed on Jun. 12, 2015.

(51) Int. Cl.
*A61H 31/00* (2006.01)
*A61B 5/021* (2006.01)
(Continued)

(52) U.S. Cl.
CPC .......... *A61H 31/005* (2013.01); *A61B 5/021* (2013.01); *A61B 5/02416* (2013.01);
(Continued)

(58) Field of Classification Search
CPC ...... A61H 7/001; A61H 31/00; A61H 31/004; A61H 31/005; A61H 31/006; A61H 31/007; A61H 2031/001; A61H 2031/002; A61H 2031/003; A61H 2201/50; A61H 2201/5007; A61H 2201/5012; A61H 2201/5015; A61H 2201/5043; A61H 2201/5048; A61H 2201/5071; A61H 2201/5058; A61H 2201/5064; A61H 2201/5061; A61H 2201/5076; A61H 2201/5084; A61H 2201/5089; A61H 2201/5092; A61H 2205/084; A61H 2230/04; A61H 2205/045; A61H 2205/08;
(Continued)

(56) References Cited

U.S. PATENT DOCUMENTS 5,496,257 A * 3/1996 Kelly .................. A61H 31/005
600/454
7,190,999 B2 3/2007 Geheb et al.
(Continued)

*Primary Examiner* — Colin W Stuart
(74) *Attorney, Agent, or Firm* — Mintz Levin Cohn Ferris Glovsky and Popeo, P.C.

(57) ABSTRACT

A system for assisting with a cardiopulmonary resuscitation (CPR) treatment being administered to a patient. In one aspect, a system for assisting with a cardiopulmonary resuscitation (CPR) treatment being administered to a patient includes a sensor for determining a parameter of the patient (e.g., indicative of a blood flow or pressure waveform), and one or more processors configured for receiving input from the sensor, determining, based on the input from the sensor, whether a rate of chest compressions administered in the CPR treatment should be changed, and providing an indication to a user that the rate of chest compressions should be changed.

37 Claims, 9 Drawing Sheets

(51) Int. Cl.
*A61B 5/024* (2006.01)
*A61B 5/00* (2006.01)

(52) U.S. Cl.
CPC ......... *A61B 5/4836* (2013.01); *A61H 31/007* (2013.01); *A61H 2201/5012* (2013.01); *A61H 2201/5015* (2013.01); *A61H 2201/5043* (2013.01); *A61H 2201/5048* (2013.01); *A61H 2201/5071* (2013.01); *A61H 2230/04* (2013.01); *A61H 2230/08* (2013.01); *A61H 2230/207* (2013.01); *A61H 2230/25* (2013.01); *A61H 2230/30* (2013.01)

(58) Field of Classification Search
CPC ........ A61H 2205/085; A61H 2205/207; A61H 2205/208; A61H 2205/25; A61H 2205/255; A61H 2205/30; A61H 2205/305
See application file for complete search history.

(56) References Cited

U.S. PATENT DOCUMENTS

| | | | | |
|---|---|---|---|---|
| 8,942,803 | B1* | 1/2015 | Herken | A61N 1/3925 607/5 |
| 10,420,701 | B2* | 9/2019 | Freeman | G06T 7/50 |
| 2004/0116969 | A1 | 6/2004 | Owen et al. | |
| 2006/0094991 | A1* | 5/2006 | Walker | A61H 31/004 601/41 |
| 2006/0229680 | A1* | 10/2006 | Chapman | A61N 1/3925 607/5 |
| 2008/0171311 | A1* | 7/2008 | Centen | G09B 23/288 434/265 |
| 2012/0010543 | A1* | 1/2012 | Johnson | G06F 19/3481 601/41 |
| 2012/0330199 | A1* | 12/2012 | Lurie | A61H 9/0078 601/41 |
| 2012/0330200 | A1* | 12/2012 | Voss | A61H 31/004 601/41 |
| 2014/0024979 | A1* | 1/2014 | Radbourne | A61H 31/00 601/43 |
| 2014/0039291 | A1* | 2/2014 | Freeman | A61B 5/4848 600/380 |
| 2015/0216447 | A1* | 8/2015 | Colman | A61B 5/7275 600/532 |
| 2016/0206504 | A1* | 7/2016 | Giarracco | A61B 5/0261 |

* cited by examiner

ASSISTING A CPR TREATMENT

CROSS-REFERENCE TO RELATED APPLICATION

This application claims benefit of priority to U.S. Provisional Application Ser. No. 62/175,086, filed on Jun. 12, 2015, the entire contents of both are hereby incorporated by reference.

TECHNICAL FIELD

This document relates to assisting a cardio-pulmonary resuscitation (CPR) treatment, including systems and techniques for optimizing the effectiveness of CPR by changing the rate of chest compressions.

BACKGROUND

CPR is a treatment for patients experiencing cardiac arrest in which chest compressions and ventilation is applied to the chest of a victim. According to American Heart Association Guidelines for Cardiopulmonary Resuscitation and Emergency Cardiovascular Care, it is recommended to perform CPR at a constant compression rate of 100 chest compressions per minute (cpm) and at a compression depth of about 4-5 cm. Commercially available CPR feedback devices, as well as mechanical chest compression devices, typically implement the AHA recommended protocols.

SUMMARY

In one aspect, a system for assisting with a cardiopulmonary resuscitation (CPR) treatment being administered to a patient includes a sensor for determining a parameter (e.g., indicative of a blood flow or pressure waveform) of the patient, and one or more processors configured for receiving input from the sensor, determining, based on the input from the sensor, whether a rate of chest compressions administered in the CPR treatment should be changed, and providing an indication to a user that the rate of chest compressions should be changed.

In another aspect, a system for assisting with a cardio-pulmonary resuscitation (CPR) treatment being administered to a patient includes a timer module configured to determine an amount of time elapsed since chest compressions are commenced, and one or more processors configured for determining, based on the amount of time elapsed, whether a rate of chest compressions administered in the CPR treatment should be changed, and providing feedback for a user of the system indicating that the rate of chest compressions should be changed.

In another aspect, a system for assisting with a cardio-pulmonary resuscitation (CPR) treatment being administered to a patient including a sensor for measuring a parameter (e.g., indicative of a blood flow or pressure waveform) of the patient, a metronome to guide a user in applying chest compressions at a first rate, a motion sensor configured to measure rate of compressions exerted by the user on the patient, one or more processors configured for receiving input from the sensor and the motion sensor, determining, based on the input from the sensor, whether a rate of chest compressions administered in the CPR treatment should be changed, a user interface module, wherein the user interface module is configured to provide feedback indicating that the rate of chest compressions is to be changed, and providing a second rate to guide the user in applying chest compressions.

In a further aspect, a system for assisting with a cardiopulmonary resuscitation (CPR) treatment being administered to a patient comprises one of a timer module configured to determine an amount of time elapsed since chest compressions are commenced or a sensor configured to determine a blood flow or pressure feature or metric, a mechanical chest compression device, a mechanical chest compression device controller, and one or more processors configured for instructing the mechanical chest compression device controller to provide chest compressions at a first rate, determining, based on the amount of time elapsed or the sensed parameter, whether a rate of chest compressions administered in the CPR treatment should be changed, and providing a second rate of chest compressions based on the time elapsed.

In other aspect, a method for assisting with a cardiopulmonary resuscitation (CPR) treatment administered to a patient includes receiving, by one or more processors, an input from a sensor measuring a waveform indicative of at least one of a blood flow, a pulse wave velocity or a blood pressure of the patient, determining, by one or more processors and based on the input from the sensor, that a rate of chest compressions administered in the CPR treatment should be changed, and providing, by one or more processors, a feedback indicating that the rate of chest compressions should be changed.

The details of one or more implementations are set forth in the accompanying drawings and the description below. Other features and advantages will be apparent from the description, drawings, and claims.

DETAILED DESCRIPTION

A person who is attempting to use chest compressions to rescue a patient applies a force to the patient's chest as part of the CPR treatment. The person (whom we sometimes call a rescuer, or user) sometimes uses a device to assist with the CPR treatment. Among other functionality, the device can provide feedback to the rescuer about the rate at which the rescuer should apply the chest compressions. Typically, the feedback devices, such as those available commercially today, provide feedback to the rescuer based on the chest compression rate recommended by the AHA. However, it may be advantageous to provide an optimized rate (e.g., a rate that is most likely to contribute to rescue the patient) over the course of the treatment. Thus, a feedback device can be configured to adjust the compression rate over the course of the CPR treatment. The adjustment in compression rate can be based on the time since CPR was started or based on a particular parameter. In various embodiments, blood flow or pressure features or metrics are used to adjust the rate of chest compressions. Examples of such features or metrics include vascular response, flow volume, flow velocity, blood pressure, etc. The amount of time elapsed since the CPR treatment commenced may also be used to adjust the compression rate.

Figure 1:
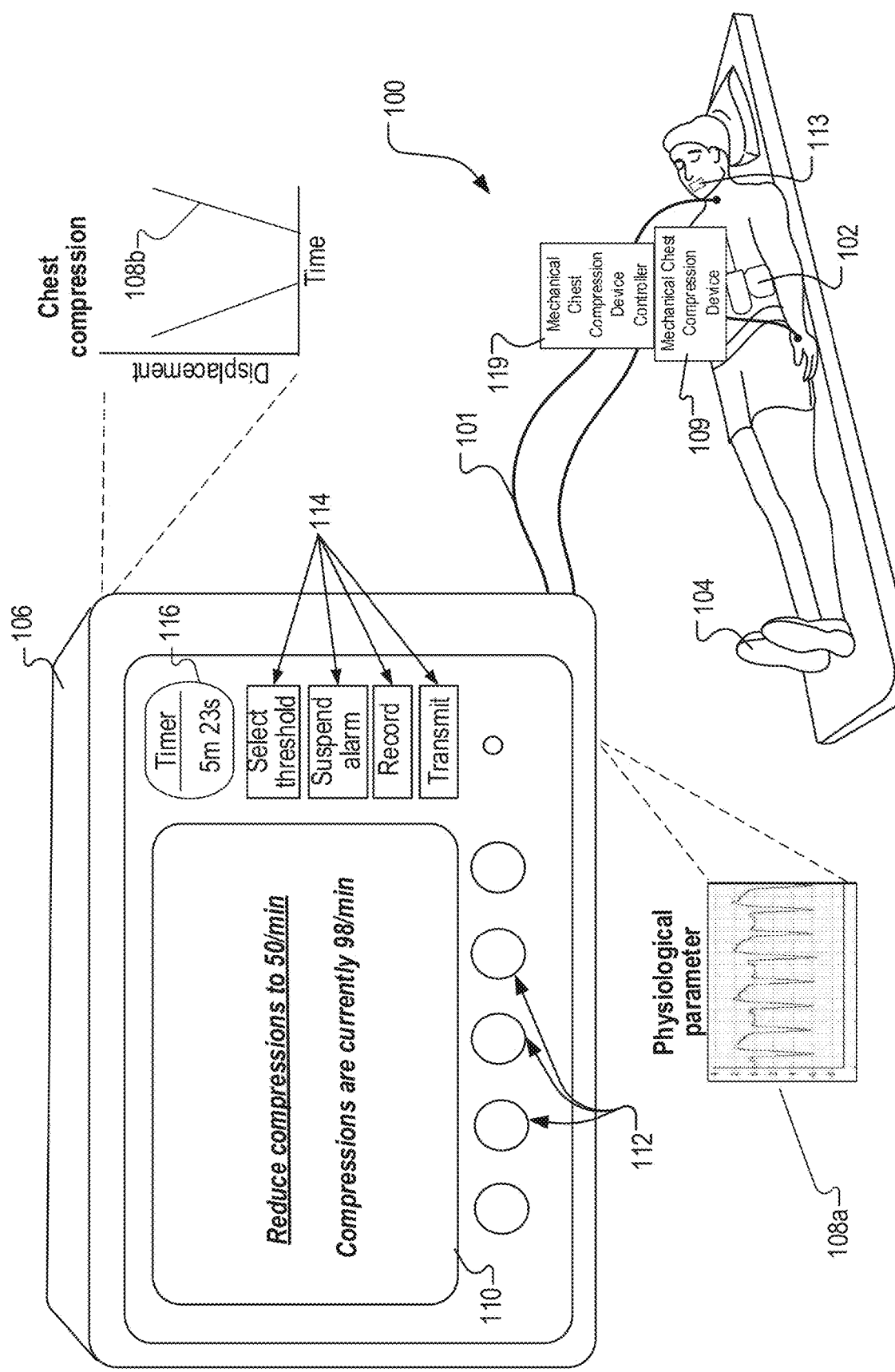
FIG. 1 is a schematic illustration of an example system for assisting with CPR treatment.

FIG. 1 illustrates an example patient monitoring configuration 100. The patient monitoring configuration 100 includes one or more sensors 101 and 102 that can be attached to various locations on the body surface of the patient 104. The sensors 101 and 102 are electrically coupled to a patient monitoring device 106 which provides output 111 on a user interface 110 based on input received from the sensors. The output can include directions to a user of the monitoring device 106 (e.g., directions specifying a rate of chest compressions to administer to the patient 104).

In some examples, the sensors 101 and 102 can include a sensor for measuring a parameter indicative of a blood flow or pressure waveform of the patient 104 and a CPR sensor for determining the rate and/or depth of chest compressions. In some implementations, the blood flow or pressure waveform features or metrics can include a vascular parameter, such as a blood flow, a pulse wave velocity, a blood pressure, flow velocity, etc. In some implementations, the sensor can be a tonometer, a laser Doppler blood flow sensor, an ultrasound Doppler blood flow sensor, a blood pressure sensor, and/or other sensor for measuring a blood flow or pressure waveform feature or metric. In some implementations, the sensor(s) 102 used to determine and/or provide feedback relating to chest compression rate can include a motion sensor (e.g., accelerometer or magnetic flux motion sensor), which may be configured to analyze motion signals such as an accelerometer signal that may be used to provide measures of compression depths and compression rates exerted by the user of the system 100.

The portion of the body surface of the patient 104 selected for attaching the sensors 101 that monitor a parameter indicative of a blood flow or pressure waveform responsive to CPR can depend on the type of the selected sensor or sensors and the imaging target (e.g., inferior vena cava, carotid artery, jugular vein, renal artery, brachial artery, femoral artery or abdominal aorta). Example portions of the body surface of the patient 104 that can be selected for attaching the sensors 102 include the chest, the neck, the abdomen, the limb of the patient 104, etc.

The sensors 101 and 102 can be electrically coupled to the patient monitoring device 106. An example of a patient monitoring device 106 can be a standard CPR monitoring device, a portable CPR monitoring device, a defibrillator, a smartphone, a personal digital assistant (PDA), a laptop, a tablet personal computer (PC), a desktop PC, a set-top box, an interactive television, and/or combinations thereof or any other type of medical device capable to record and process CPR signals and parameters. For example, the sensors 101 and 102 can be implemented in or coupled to standard medical devices, such as X-Series monitors and defibrillators produced by ZOLL Medical®, Chelmsford MA. In some implementations, the patient monitoring device 106 communicates with an external device (e.g., a device that can operate independent of the patient monitoring device 106). For example, the external device may include user interface functionality, and information communicated by the patient monitoring device 106 can be provided to a user by way of the user interface functionality (e.g., displayed on a display). The external device can be any appropriate device, such as a laptop, tablet computer, smartphone, smartwatch, or any of the other electronic devices mentioned above.

In the illustrated example, the patient monitoring device 106 is configured to display a feedback to the user. The feedback can include a substantially real-time report of the ongoing CPR and/or a recommendation to modify the CPR protocol (e.g., chest compression rate). The feedback can based on a parameter 108a and a chest compression waveform 108b that are acquired via the sensors 101 and 102 and processed by the device 106. The parameter 108a can depict vascular tone of the patient undergoing CPR treatment (e.g., using a mechanical chest compression device 109 including a mechanical chest compression device controller 119 and a mechanical ventilation unit 113). Examples of such parameters 108a can include blood flow, pulse wave velocity, blood pressure in a particular artery, etc. The chest compression waveform 108b can depict the variation of compression displacement and compression rate (for example, a numerical value of the average compression rate determined for a window of chest compressions) over time.

The monitoring device 106 enables user input via the user interface 110 and additional control buttons 112 and 114. In some implementations, the control buttons 112 can enable a user to select one of a plurality of available modes (e.g., display modes, or other types of output modes, such as audio output modes) of the user interface 110. In some implementations, the graphical user interface 110 can be configured to operate in one of multiple modes, depending on the level of sophistication of the user of the monitoring device 106. For example, a first mode can be tailored to a medical professional with any level of training, or a non-medical professional, and may not display detailed data (e.g., data received from the sensors such as data describing the parameter 108a). Instead, the first mode can provide plain-language instructions that would be understandable by a medical professional or a non-medical professional, such as the instructions shown in the output 111.

A second mode of the graphical user interface 110 can provide more detailed information, such as information that may be of interest to a medical professional having a training about data provided by the sensors 102. The second mode can include the display of the parameter 108a indicative of the blood flow or pressure waveform and/or the chest compression waveform 108b. For example, the parameter 108a and the chest compression waveform 108b may be used by a clinician in administration and optimization of CPR treatment.

In some implementations, the control buttons 114 can enable a user to initiate, stop or modify particular actions that can be performed by the patient monitoring device 106. Actions that can be initiated, stopped or modified by using the buttons 114 can include the selection of processing method, selection of an alarm threshold, suspension of alarm, recording of data, and transmitting data over the network to a remote device. In general, the user interface 110 can be implemented by one or more modules of the monitoring device 106 (e.g., physical devices including processors, software such as executable code, or a combination of both).

In some implementations, the monitoring device 106 can also include a timer (or metronome) 116 (e.g., as a module of a microprocessor or microcontroller of the monitoring device 106). The timer 116 can enable a user of the device 106 to monitor an amount of time elapsed since the CPR treatment commenced. The initiation of time recording can be triggered by a user interacting with the device 106, by identifying start of CPR based on the received chest compression waveform 108b or detecting chest displacement, by detecting the deployment of a defibrillator, etc. For example, a compression displacement, which is proportional to the compression force applied by the rescuer 105, 107 on the patient's chest, that is different than 0 cm can be used as an indicator that CPR was initiated.

The monitoring device 106 can also include a rate indicating prompt (e.g. a metronome) and/or audible, visual or text instructional prompts to perform chest compressions at a given compression rate or with a particular timing. For example, the user can be initially prompted with the use of a metronome (e.g., a rate indicating prompt) and/or audible instructional prompts to perform CPR at a specific rate, (e.g., according to AHA guidelines, such as 100 cpm with 4-5 cm compression depths). Audible prompts may take the form of verbal messages such as, "Press Faster" or a particular tone that indicates that the correct rate or timing has been achieved, for instance a "Ping" sound for when the correct rate or timing has been achieved and a "Thud" sound for when the rate is incorrect. An example of a text prompt might be "Press Faster" or "Press slower" appearing on a display of a defibrillator that provides CPR coaching. An example of a visual prompt might be a numeric value of the compression rate; it might also be an up or down arrow indicating for the rescuer to press faster or slower, respectively. Based on the recorded parameter 108a indicative of the blood flow or pressure waveform or the time elapsed and the chest compression waveform 108b, the compression rate and/or compression depth can be altered from the recommended guideline via the metronome and voice prompts to improve circulation. For example, the feedback control system via the metronome and audible prompts can assist the user in manually changing the compression rate or authorizing an automatic change of the compression rate, as described with reference to FIGS. 3 and 4. In implementations where chest compressions are delivered by a mechanical device, such as a belt driven or piston based chest compression device, the compression rate may be modified based on a parameter indicative of the blood flow or pressure waveform, based on elapsed time, or a combination of both.

In some implementations, the user can be prompted by the monitoring device 106 to perform CPR at a particular compression rate. The user may be provided additional prompts, for example, relating to the compression depth (e.g., to push harder or softer), to fully release the chest, etc. For example, if the monitoring device 106 has determined that the chest is not being compressed to the AHA recommended depth of 4-5 cm or not being completely released at the end of each compression the device may prompt the user to correct his or her chest compression depth and/or release.

The monitoring device 106 can also have audio capability. For example, based upon detection of a particular CPR condition, the monitoring device 106 can issue audible prompts instructing the rescuer to decrease compression rate, to stop compressions for a brief period or to deliver one or several rescue breaths. The monitoring device 106 can prompt the rescuer to resume chest compressions at an updated compression rate as it monitors compression rate and parameters indicative of blood flow or pressure (e.g., vascular response, blood flow, etc.) to estimate the success of CPR efforts and the device may provide further prompts related to compression rate, depth, and breathing. In another example, the monitoring device may prompt the rescuer to provide the AHA recommended compression rate at the beginning of CPR and gradually decrease the rate of chest compressions as a function of lapsed time. For example, the rescuer may be prompted to decrease the compression rate to from about 100 compressions per minute (cpm) to about 75 cpm. As CPR progresses the rescuer may be prompted to decrease compression rates further based on the monitored parameter(s), for example, to about 50 cpm.

Figure 2:
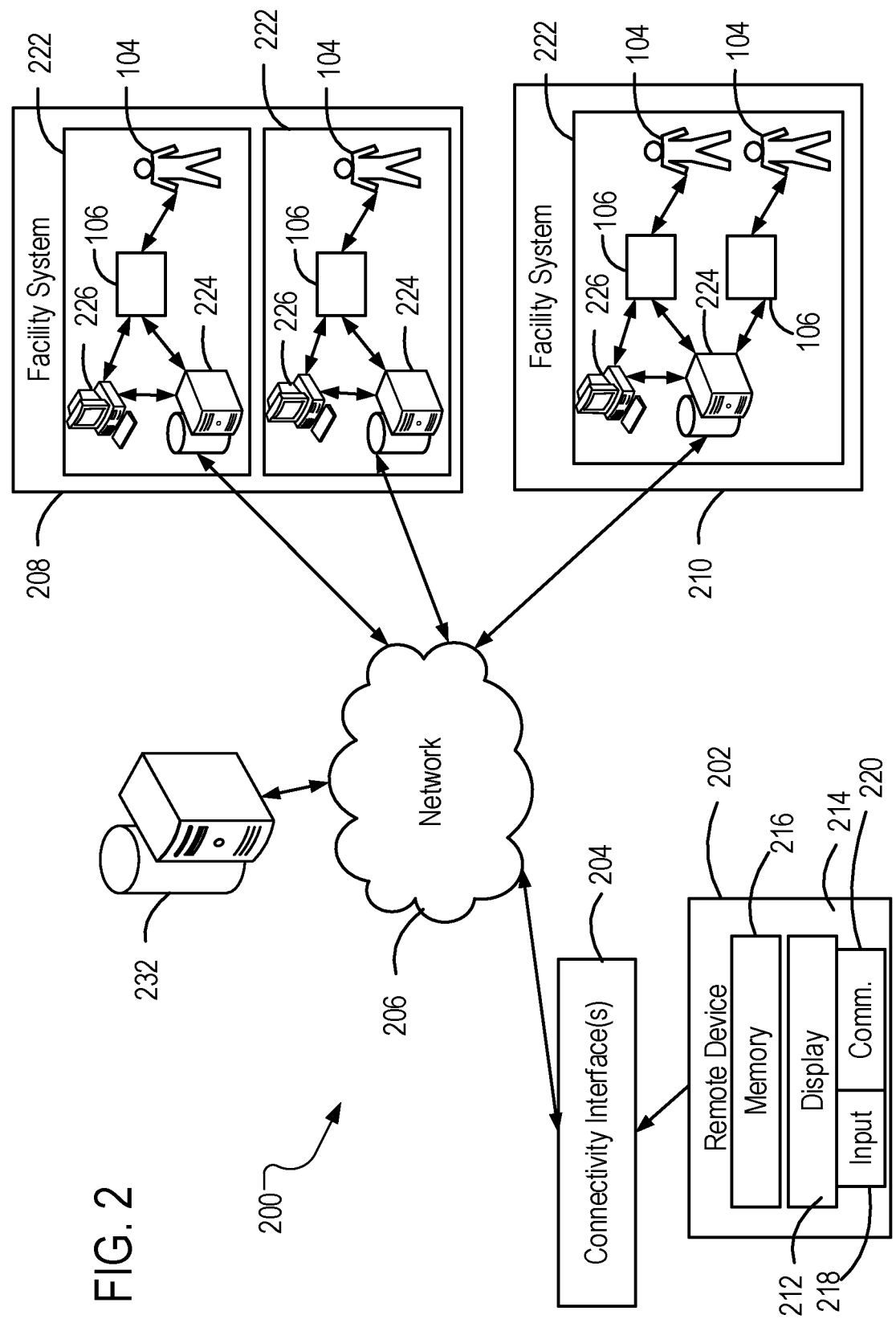
FIG. 2 is a schematic illustration of another example system for assisting with CPR treatment.

FIG. 2 shows an example system 200 that includes CPR monitoring processes, including identification of a trigger to optimize a CPR treatment. The cardio-vascular activity of a patient can be continuously monitored by the patient monitoring device 106, which includes an arterial monitoring device and/or a timer. The patient monitoring device 106 can include a patient information system 224 and a computer interface 120, forming a system for indicating that the rate of chest compressions should be changed to an optimized rate. The optimized rate corresponds to a CPR treatment with an increased probability of success by promoting an increase in cardiac output.

The system 200 for indicating that the rate of chest compressions should be changed to an optimized rate can provide changes that can occur automatically upon the identification of an event (e.g., detection of a parameter feature and/or value of blood flow or pressure or temporal threshold). Different facility systems 208 and 210 may process input data according to different rules. For example, in some cases, patient data is transferred to a remote device 202 at the identification of an event (e.g., detection of a parameter feature and/or value of blood flow or pressure). In other cases, data can be transferred upon a request of a user of the remote device 202.

The remote device 202 can include, but are not limited to, a mobile phone, a smartphone, a personal digital assistant (PDA), a laptop, a tablet personal computer (PC), a desktop PC, a set-top box, an interactive television, and/or combinations thereof. The remote device 202 includes a display 212, a processor 214, memory 216, an input interface 218, and a communication interface 220.

The remote device 202 can communicate wirelessly through the communication interface(s) 204, which can include digital signal processing circuitry. The communication interface(s) 204 can provide communications under various modes or protocols including, but not limited to, GSM voice calls, SMS, EMS or MMS messaging, CDMA, TDMA, PDC, WCDMA, CDMA2000, and/or GPRS. Such communication can occur, for example, through a radio-frequency transceiver (not shown). Further, the remote device can be capable of short-range communication using features including, but not limited to, Bluetooth and/or WiFi transceivers (not shown).

The remote device 202 communicates with the network 206 through the connectivity interface(s) 204. The connectivity interface(s) 204 can include, but is not limited to, a satellite receiver, cellular network, a Bluetooth system, a Wi-Fi system (e.g., 202.x), a cable modem, a DSL/dial-up interface, and/or a private branch exchange (PBX) system. Each of these connectivity interfaces 204 enables data to be transmitted to/from the network 206. The network 206 can be provided as a local area network (LAN), a wide area network (WAN), a wireless LAN (WLAN), a metropolitan area network (MAN), a personal area network (PAN), the Internet, and/or combinations thereof.

In the systems of FIG. 2, the first facility system 208 includes a plurality of facilities 222, and the second facility system 210 includes a single facility 222. Each facility 208, 210 or 222 includes an associated patient information system 224, computer system(s) 226, and patient monitoring device(s) 106. In some implementations, the patient information system 224 can include a cardiology information system. Although the system architecture 200 includes a patient information system 224 located at each facility 222, it is contemplated that the facilities 222 can communicate with a common patient information system 224 that is remotely located from either facility 222, or that is located at one of the facilities 222 within the facility system 208, 210.

Each patient monitoring device 106 is configured to monitor physiological characteristics of a particular patient 104, to generate data signals based thereon. For example, the patient monitoring devices 208 include CPR monitoring devices, monitoring devices for physiological parameters, and one or more processors. The data signals are communicated to the patient information system 224 which can collect patient data based thereon, and store the data to a patient profile that is associated with the particular patient. The patient monitoring device 106 can communicate with the patient information system 224 and/or the computer interface 120 via a direct connection, or remotely through a network (not shown) that can include, but is not limited to, a LAN, a WAN, a WLAN, and/or the Internet.

In some cases, the patient data can include CPR waveforms, physiological parameters, data extracted from the processed physiological parameters (e.g., portion of physiological parameter and indicator) and, optionally, additional coregistered physiological data. The patient data can be made available for display on remote device 202 and/or directly at the patient monitoring device 208. A healthcare provider (e.g., a technician, a nurse, and/or physician) can augment the patient data by inputting patient information that can be stored by a patient information system 224. More specifically, the healthcare provider can input patient information corresponding to a particular patient 104, which patient information can be stored to the patient profile. A healthcare provider can also provide instructions to the remote rescuer to modify the CPR treatment, for example, by changing the rate of chest compressions.

As discussed above, each patient information system 224 stores patient data that can be collected from the patient monitoring devices 106, as well as additional patient information, that can include information that is input by a healthcare provider. The patient information system 224 communicates the patient data and/or the additional patient data to a server 232, or a virtual server that runs server software components, and can include data storage including, but not limited to, a database and/or flat files. Each patient information system 224 communicates with the server 232 via a direct connection, or remotely through a network (not shown) that can include, but is not limited to, a LAN, a WAN, a WLAN, and/or the Internet.

The server 232 can communicate ancillary information (e.g., treatment plan) to the patient information system 224. In some implementations, each facility system 208, 210 can include a corresponding server 232. In such an arrangement, each patient information system 224 communicates patient data, and/or additional patient data to the server 232. The example system architecture of FIG. 2, provides for the remote location of data collection at the server 232. In such implementations, the server 232 can be provided at a third-party site, remote from any of the facilities 222, or facility systems 208, 210.

Figure 3:
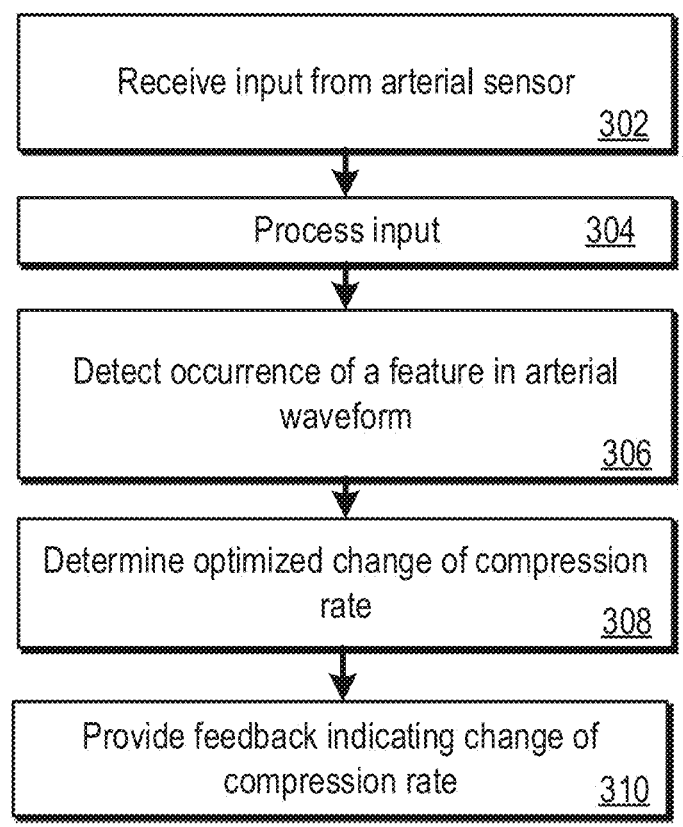
FIG. 3 is a flow chart of an example process for assisting with CPR treatment.

FIG. 3 shows an example process 300 for assisting with CPR treatment based on identification of a feature of the parameter(s) indicative of a blood flow or pressure waveform of the patient. In some examples, the method 300 can be implemented by the patient monitoring device 106 described above with reference to FIGS. 1 and 2. However, other implementations are possible.

At a step 302, a patient is monitored by recording one or more types of parameters, including an arterial waveform. The parameter can be received from any appropriate source of patient parameter. For example, the parameter can be received substantially in real-time from an a tonometer, a laser Doppler blood flow sensor, a blood pressure sensor, or another sensor for measuring blood flow or pressure waveforms. The parameter can be of any appropriate type. The parameter can be recorded from a plurality of sites on the surface of the patient's body, such as inferior vena cava, carotid artery, renal artery, brachial artery, femoral artery, and/or abdominal aorta. In some implementations, blood flow, pulse wave velocity, and/or blood pressure can be derived based on signals retrieved with the arterial sensors, such as that in graphs illustrated in FIGS. 6A-6E.

In some implementations, information about the source of the parameter for determining a blood flow or pressure waveform can be provided to a patient monitoring device (e.g., the patient monitoring device 106 shown in FIG. 1). For example, the patient monitoring device can adapt the configuration of the display and/or analysis tools based on the source of the parameter, such that the axis labels and ranges enable optimal visualization. In some implementations, the parameter indicative of the blood flow or pressure waveform is received together with additional patient data, including the depth and rate of chest compressions exerted by the user on the patient, other physiological data recordings, medical history, physical exam findings, and other medical information that might be requested by a user. Patient data can be used in conjunction with patient-specific physiological parameter for data processing and display, or it can be used to correlate information extracted from the measured parameters. In some cases, physiological parameters measured from sensors other than those used to determine the blood flow or pressure waveform of the patient may be used to guide resuscitative therapy.

At step 304, a parameter indicative of the blood flow or pressure waveform is determined based on the signal received from an arterial sensor. The parameter provides a time-dependent indication of the cardiac output and/or blood flow. Multiple parameter sites for determining the blood flow or pressure waveform can provide different time-dependent parameters that each reflect cardiac output and/or blood flow. For example, a change in the cardiac output can appear more pronounced in a parameter measured at a particular site (e.g., inferior vena cava).

Additionally, at step 304, the patient monitoring device can perform parameter pre-processing substantially in real time. Real time parameter pre-processing can include removing the DC component with a high-pass filter, amplifying the measured parameter(s), limiting the signal bandwidth with a low-pass filter and digitally sampling the measured parameter(s). It will be appreciated that the processing will provide an indication of cardiac output and/or blood flow substantially in real-time, including within a meaningful time to allow a user and/or mechanical chest compression device to modify chest compression rates, if needed.

Figure 6B:
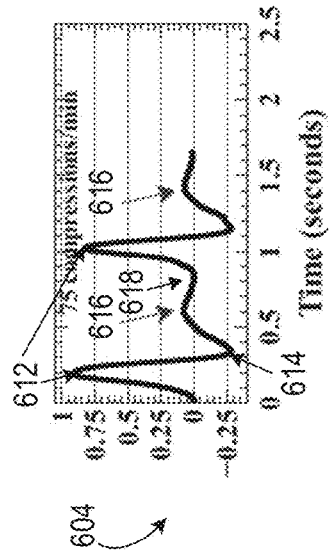
FIGS. 6A-6E are plots of carotid flows obtained from porcine models administered according to various compression rates during resuscitation.
Figure 6D:
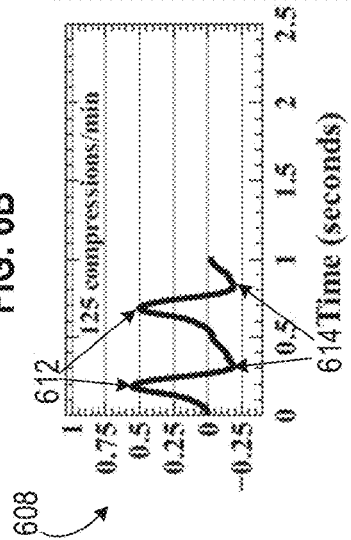
Figure 6A:
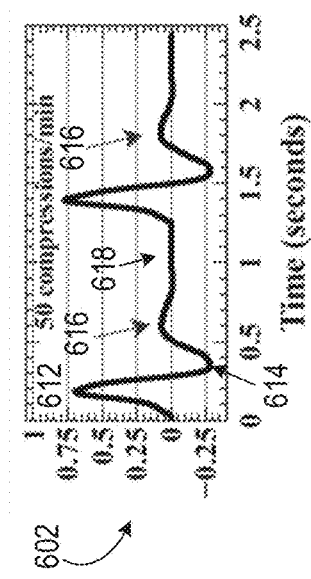
Figure 6C:
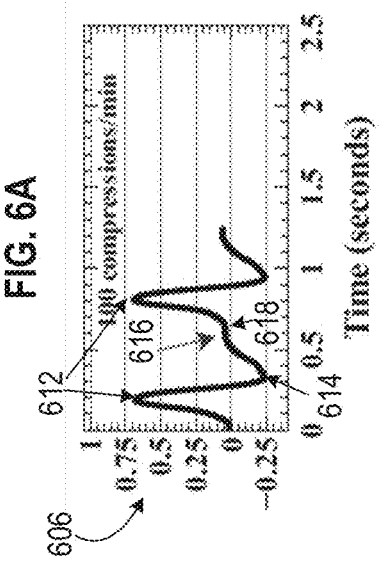

At a step 306, the process determines the occurrence of a feature in a portion of the parameter(s), for example a feature in an arterial or venous flow or pressure waveform, such as a local maximum 616 showing a notable increase in arterial flow volume, as illustrated in FIGS. 6A-6C. In some implementations, the determined feature or the absence of a feature (such as the absence of a period of increased flow) is indicative of a change (e.g., reduction) in arterial flow, blood pressure, and/or backward flow. The portion of the arterial or venous waveform can correspond to the systolic and/or diastolic phase.

For example, where the arterial (or venous) waveform is monitored, identifying a portion of the waveform can include determining an onset of a chest compression and an end of the compression (e.g., the onset of compression down-stroke and end of upstroke). Other fiducial points may also be used to determine a portion of the waveform to be analyzed. In some implementations, each waveform portion to be analyzed is determined based on a simultaneously recorded ECG.

In some implementations, the information about a plurality of waveform portions is used to calculate a reference portion and store the reference portion. In some implementations, statistical shape analysis can be used to characterize the waveform or groups of waveforms. For example, a reference portion can be generated automatically at the beginning of the CPR treatment session or it can be obtained based on a database of waveforms. The patient monitoring device can be configured to receive a user input on that allows the user to manually initiate a new acquisition of the reference portion and/or the monitored portion. The reference portion can be determined for two or more waveforms corresponding to different arterial or venous targets (e.g., inferior vena cava, carotid artery, jugular vein, renal artery, brachial artery, femoral artery, abdominal aorta, etc.). In some implementations, the reference portion can be determined as described above, or it can correspond to 30 seconds up to 3 minutes. The time period can be configured in the non-volatile storage memory of the patient monitoring device.

In some implementations, statistical shape analysis can be employed. Such shape analysis includes methods for studying the geometrical properties of objects, such as a waveform. The constraints can be determined from historical data (e.g., by machine learning) giving the model flexibility, robustness and specificity as the model synthesizes plausible instances with respect to the observations. In order to determine whether an object (e.g., a waveform portion, or feature of the waveform) has changed shape, the shape of the object is first determined. In addition to using the shape analysis of a waveform portion, other parameters can be used in the analysis, for example, a landmark, an anatomical landmark, mathematical landmarks, etc.

Analysis of the baseline and/or reference portion (or value) of one or more parameters in comparison to the monitored portion (or value) of the one or more parameters can be determined substantially in real-time. Such analysis can be used to determine a decrease of cardiac output or blood flow. The occurrence of a decrease of cardiac output and/or blood flow can be calculated by a variety of methods. In some examples, the decrease of cardiac output and/or blood flow can be determined based on a mathematical model, such as one based on logistic regression. Exemplary logistic regression models that can be used include univariate analysis or multivariate non-linear regression.

In one implementation, the identification of the decrease of cardiac output and/or blood flow can be determined at regular intervals such as 10 seconds, 30 seconds, or 1 minute. The logistic model can take into account the first, second and higher order derivatives of the shape distance between the first and second portions of parameters indicative of the blood flow or pressure waveform (e.g., an arterial or venous waveform). In other words, if the distance is diverging more rapidly, that is a sign of the patient's condition degenerating more rapidly and this in itself can indicate the decrease in cardiac output and/or blood flow. An analysis, such as a statistical one, is performed on parameter trajectories for multiple compression cycles. The analysis can be used to determine whether cardiac output and/or blood flow is decreasing or increasing.

In some implementations, the analysis can be based on an average or median of a value of a parameter indicative of the blood flow or pressure waveform corresponding to a plurality of compression cycles. In some implementations, the average or median of a value of a parameter obtained from within the previous 5 seconds up to 10 minutes from present time can be used. The time period, from which the average or median of the value of the parameter is determined, can be separated by at least 5 seconds from the time period corresponding to a reference period (e.g., obtained at the beginning of CPR or from a patient database).

The analysis of a new set of test parameters indicative of the blood flow or pressure waveform can be based on a time threshold (e.g., a new set of parameters is analyzed every 3 minutes or every 30 minutes) or can be based on a trigger such as the start of a new compression cycle (e.g., corresponding to multiple compressions). A parameter value and/or feature is determined for a particular compression that can be included in the set of test parameters indicative of the blood flow or pressure waveform. The system can monitor the length of time for which the one or more parameters are measured based on a predetermined criteria. For example, the size of the test set can be based on a threshold number of parameters and/or on a time based threshold. If the size of the test set has not been reached, the system continues to determine parameter values and/or features to add to the test set. If the size of the test set has been reached, the system characterizes the test set of parameters.

In some implementations, the occurrence of a feature of interest in the parameter indicative of the blood flow or pressure waveform is identified by comparing the test parameter trajectory to a control parameter trajectory. The feature can be identified based on a statistical analysis. For example, a variation of the parameter trajectory from the control parameter trajectory that occurs for a portion of the parameter and exceeds the standard deviation of the control parameter trajectory can be identified as the occurrence of the feature of interest. In some implementations, the action of arterial feature identification can include calculating an area of the parameter trajectory and subtracting the area of the parameter trajectory from an area of the control parameter trajectory.

In some implementations, the step 306 is repeated multiple times to compare the parameter or a portion of the parameter indicative of the blood flow or pressure waveform of multiple consecutive compressions of a plurality of compression cycles to determine a trend of the waveform parameter. Based on the trend, a decrease or an increase of cardiac output and/or blood flow can be identified. For example, the action of identifying an arterial feature (e.g., local maxima 616 in flow, described with reference to FIGS. 6A-6E) and monitoring the feature can be repeated (e.g., over multiple compression cycles) and/or conducted substantially continuously during CPR. For example, the occurrence of a feature and/or a value of the blood flow or pressure waveform parameter can be identified for each recorded compression cycle, after the control blood flow or pressure waveform parameter trajectory was determined.

At step 308, the system determines an optimal change of chest compression rate. The change of chest compression rate can include a decrease or an increase of chest compression rate relative to previously applied chest compression rate. The optimal change of chest compression rate can be based on the identification of the occurrence of a feature in the blood flow or pressure waveform parameter and the recorded CPR signal.

For example, if the monitored blood flow or pressure waveform parameter is characterized by a trend that indicates a gradual decrease in blood flow over multiple heart beats, during which CPR was applied using the same compression depth and rate (e.g., 100 cpm), the system can determine that the revised rate of chest compressions is a fraction of the previously applied rate (e.g., 75 cpm). In some implementations, the optimal change of chest compression rate can be proportional to the changing trend of the blood flow or pressure waveform parameter.

At step 310, the system provides feedback to the user of the device indicating the revised compression rate. For example, the feedback can be provided by a user interface module (e.g., implementing the user interface 110 of FIG. 1). In some implementations, the indicator can include a visual display on the monitoring device based on the identification of the occurrence of a feature in the blood flow or pressure waveform parameter and, in some implementations, an alarm alerts a user of the device about the occurrence of the feature. In some implementations, both the metronome rate and the compression prompts can be used simultaneously to guide the user in applying CPR. In other implementations a mechanical chest compression device can be reset to a revised compression rate.

The example process 300 can be repeated multiple times until the completion of CPR treatment. For example, if compression characteristics match the defined level and a blood flow or pressure waveform parameter is measured and it indicates optimal vascular tone, CPR can be considered adequate and no changes to the metronome and/or additional voice prompts are generated. As another example, if compression characteristics match the previously defined optimal level (at step 308) and an arterial or venous waveform is measured and it indicates a decrease in vascular tone, CPR can be considered inadequate. In response to determining that CPR protocol is inadequate, a revised rate of chest compressions can be determined and the user can be prompted to modify CPR based on the newly identified rate of chest compressions.

Figure 4:
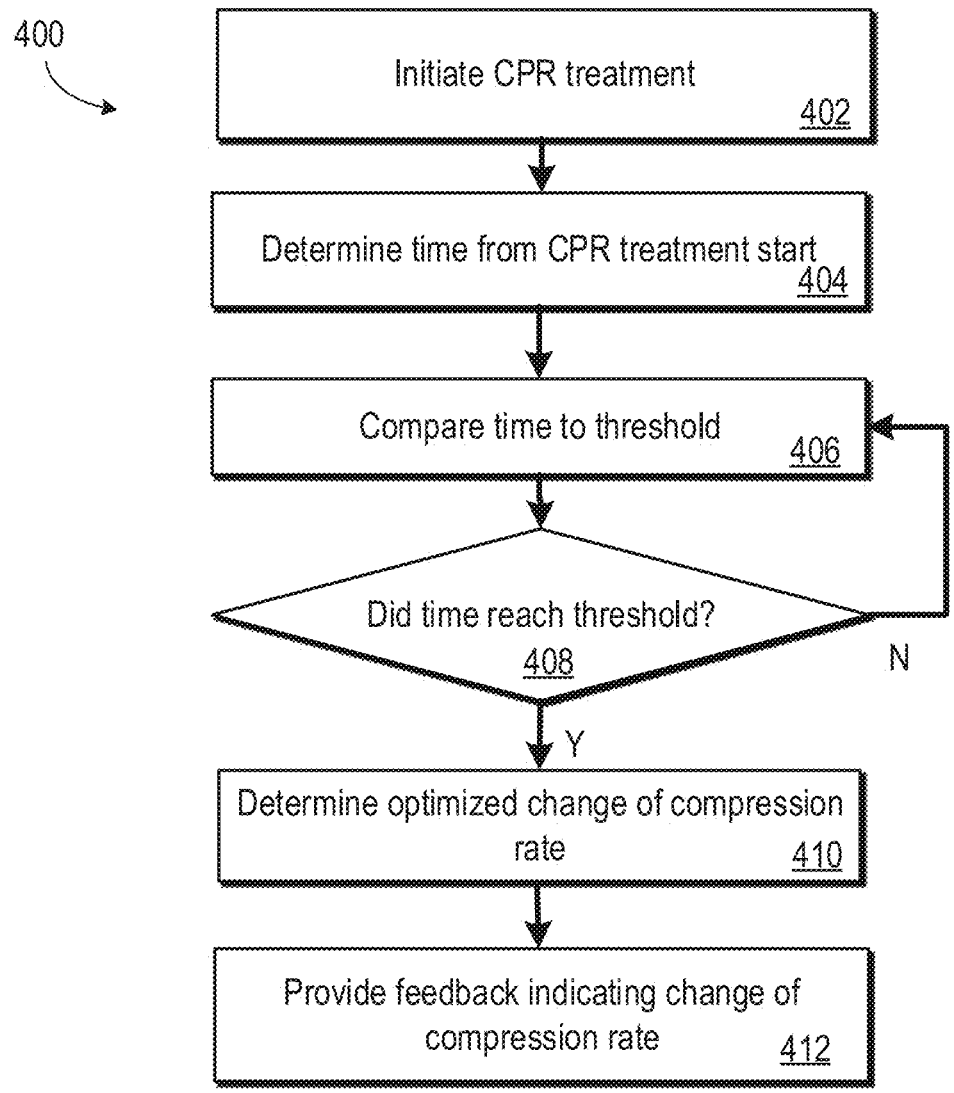
FIG. 4 is a flow chart of another example process for assisting with CPR treatment.

FIG. 4 shows an example process 400 for assisting with CPR treatment based on identification of an amount of time elapsed since the CPR treatment commenced. In one implementation, the method 400 is implemented by the example patient monitoring device described herein with reference to FIGS. 1 and 2. However, other implementations are possible.

At a step 402, CPR treatment is initiated. For example, metronome and/or additional voice prompts are generated to guide a rescuer in applying CPR treatment at a first compression rate and depth. As another example, CPR treatment can be applied to the patient automatically using a mechanical CPR device configured to deliver mechanical CPR treatment. The device can be configured to actively compress and actively decompress the chest of the patient or to permit passive decompression of the chest of the patient at a first compression rate and depth of a variable resuscitation protocol. In some implementations, a plurality of sensors (e.g., ECG electrodes, CPR sensor, blood pressure sensor, SpO2 sensor, etc.) can be attached to the patient to monitor one or signals during CPR treatment.

At step 404, an amount of time elapsed since the CPR treatment commenced is determined. The amount of time can be determined by a timer module. The timer module can be integrated in a monitoring device (e.g., timer 116 included in monitoring device 106, as described with reference to FIG. 1), in a CPR assistance device (e.g., configured to deliver instant audiovisual feedback of compression depth and rate, complete chest recoil, hands-off time and ventilation rate), in a mechanical CPR device, in a smartphone, in a smart watch, in a personal digital assistant (PDA), in a laptop, in a tablet personal computer (PC), in a desktop PC, in a set-top box, in an interactive television and/or combinations thereof or any other type of device capable to record and process the amount of time elapsed since the CPR treatment commenced.

At a step 406, the process compares the amount of time elapsed since the CPR treatment commenced to a selected temporal threshold. The temporal threshold can be set between approximately 15 and 25 minutes. In some implementations, the threshold can be set at 20 minutes. The comparison can be performed at preset intervals (e.g., every second or every minute). In some implementations, step 406 can also include a comparison of recorded physiological signals to control physiological signals or critical ranges.

At a step 408, if the threshold has not been reached or none of the physiological signals are in critical ranges, the system continues to compare the amount of time elapsed since the CPR treatment commenced to the threshold. If the threshold has been reached, the system determines an optimal change of chest compression rate. The change of chest compression rate can include a decrease of chest compression rate to a second compression rate to the first applied chest compression rate. Optionally, the change can include a change in depth relative to the first applied compression. The optimal change of chest compression rate can be based on the amount of time elapsed since the CPR treatment commenced to the threshold. For example, the CPR treatment can include one or more changes of the compression rate based on the amount of time elapsed since the CPR treatment commenced to the threshold. If a single threshold is selected, the CPR treatment can be set to be initiated at 100 cpm and after 20 minutes to be continued at 50 cpm. If multiple thresholds are selected, the CPR treatment can be initiated at 150 cpm, after 10 minutes it can be continued at 100 cpm, and after 20 minutes it can be continued at 50 cpm.

At step 410, the system provides a feedback to the user of the device indicating the optimal change of the compression rate. In some implementations, the indicator can include a visual display on the monitoring device based on the identification of the occurrence of a feature in an arterial or venous waveform and an alarm that alerts a user of the device. In some implementations, both the metronome rate and the compression prompts can be used simultaneously to guide the user in applying CPR with identified optimal parameters.

The example process 400 can be adjusted if any of the recorded signals reaches critical ranges. For example, if a blood flow or pressure waveform feature is determined and it indicates a decrease to a critical value before the amount of time elapsed since the CPR treatment commenced reached the threshold, CPR can be considered inadequate. If the applied CPR is determined as being inadequate, a revised rate of chest compressions can be determined and the user can be prompted to modify CPR based on the revised rate of chest compressions.

Figure 5:
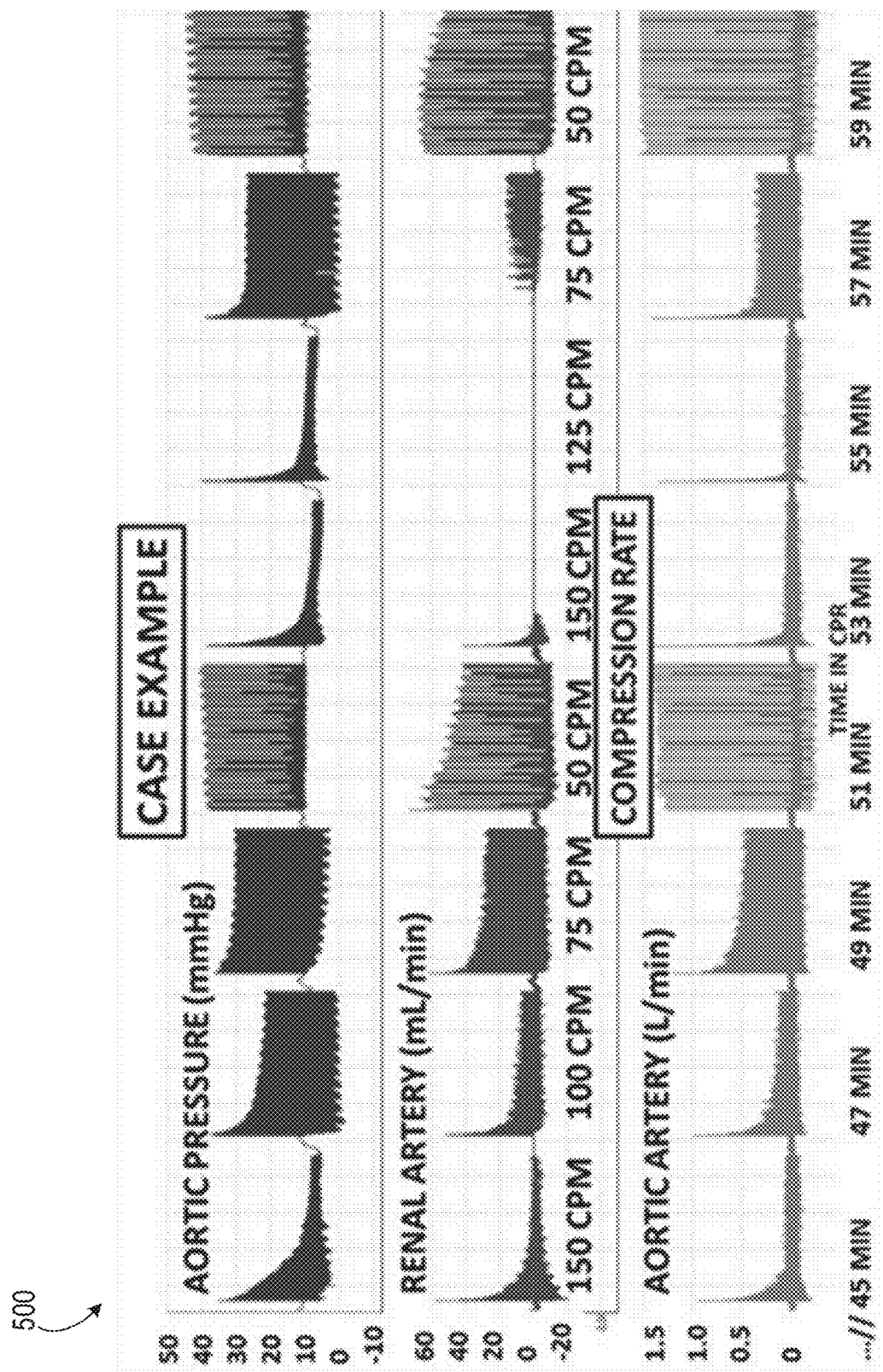
FIG. 5 is a plot of data obtained from porcine models administered various compression rates during resuscitation.

FIG. 5 shows an example illustration 500, which is not limiting of the various possible implementations that can be employed. Chest compressions were performed using a laboratory mechanical chest compression device on nine domestic porcine models (~30 Kg). Standard blood flow or pressure waveform monitoring was utilized. Blood flow was measured in the abdominal aorta (AAo), the inferior vena cava, the right renal artery and vein, the right common carotid and external jugular. Ventricular fibrillation (VF) was electrically induced. Mechanical chest compressions were started after ten minutes of VF. Chest compressions were delivered at rates of 50, 75, 100, 125, or 150 compressions per minute (cpm) and at a depth of 2" for a total of 54 min. The rates were changed every 2 min in a randomized fashion.

During the first 10 minutes of CPR, a chest compression rate of 150 cpm resulted in significantly more net AAo blood flow than a rate of 50 cpm (133.2±21.0 vs. 39.0±8.1 ml/min, $p<0.05$). During minutes 40-50 of continued compressions, a rate of 150 resulted in significantly less net AAo blood flow than a rate of 50 cpm (−1.7±4.5 vs. 13.5±5.9 ml/min, $p<0.05$). A difference in blood flow was generated on a per compression basis (ml/comp) for 150 vs. 50 cpm (−0.01±0.03 vs. 0.27±0.12 ml/comp; $p<0.05$). Referring to FIG. 5, in several porcine models, a compression rate of 150 cpm emptied the AAo and renal artery of blood while a compression rate of 50 cpm restored blood to the AAo. AAo pressure measurements confirmed the flow observations. It was found that at the onset of CPR, a compression rate of 150 cpm was significantly more effective at generating AAo blood flow than a compression rate of 50 cpm. However, after 40 minutes of compressions, reduced AAo flow and pressure resulted from higher compression rates (>125 cpm), suggesting that these rates should be avoided as resuscitation progresses.

Figure 6E:
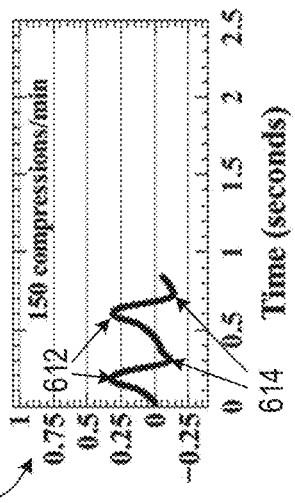

FIGS. 6A-6E are plots of blood flow volume (mL) waveforms 602, 604, 606, 608, and 610 measured in the common carotid arteries of porcine models of VF administered CPR at 50, 75, 100, 125 and 150 cpm, respectively, similar to that described with reference to FIG. 5, except these waveforms correspond to carotid flow volumes at time periods between 0-10 minutes after compressions have been initiated. Each of the displayed carotid flow volume waveforms 602, 604, 606, 608, and 610 indicates the variation in blood flow volume corresponding to the applied compression rate 50, 75, 100, 125 and 150 cpm, respectively. The blood flow volume waveforms include variations corresponding to the applied compressions. For example, the variations of the blood flow volume include a peak region 612 corresponding to each compression, a backward flow minimum 614, a local maximum 616 and a baseline region 618. Those of skill in the art may refer to the peak region as a systolic-type behavior that occurs during chest compression; similarly, the region characterized by the local maximum and baseline may be referred to as a diastolic-type behavior. Referring to FIGS. 6A-6C, each peak region 612, backward flow minimum 614, local maximum 616 and baseline region 618 can be distinguished in the blood flow volume waveforms 602, 604, and 606, respectively. That is, each of the noted features are prominently shown in the waveform for identification. Referring to FIGS. 6D and 6E, some of the above-noted features of the blood flow volume waveforms 608 and 610 are not easily distinguished from other portions of the waveform. For example, the local maxima 616 and the baseline regions 618 cannot be identified in the blood flow volume waveforms 608 and 610. It has been observed that for some cases, the amplitude of the peak region 612 and the amplitude of the backward flow minimum 614 is inversely proportional with the compression rate. For example, at times, the peak region 612 and the backward flow minimum 614 may present larger amplitudes in the mean blood flow volume waveforms 602 and 604 corresponding to the lower compression rates of 50 cpm and 75 cpm.

Upon further inspection of the blood flow volume waveforms of FIGS. 6A-6E, the waveforms 604, 606 corresponding to compression rates of 75 cpm and 100 cpm, respectively, appear to provide more favorable flow characteristics. For instance, with each compression, the peak region 612 is accompanied by a local maximum 616, indicating that additional blood is able to flow, possibly due to the occurrence of backflow reflections in a positive direction. It is noted that the waveform 602 corresponding to a compression rate of 50 cpm also includes a prominent local maximum 616, however, the baseline region 618 covers a substantially long time period before the next compression ensues. With the objective being to maximize blood flows, it is preferable for a compression to begin immediately after or during the local maximum 616 (as shown by waveforms 604, 606), rather having a relatively long delay (as indicated by the extended baseline region 618) before a subsequent compression begins. As discussed above, the waveforms 608, 610 corresponding to compression rates of 125 cpm and 150 cpm show respective peak regions 612, yet absent a local maximum 616. Depending on the amount of blood flow per compression, it may be preferable for the compressions to be timed such that the local maximum 616 appears, so as to increase overall blood flow.

It should be appreciated that the features present in the blood flow or pressure waveforms corresponding to particular compression rates will vary depending on the amount of time elapsed from when continuous compressions have been initiated. For instance, as compressions continue, for a given compression rate, the characteristics of the blood flow waveform, such as the length of the baseline region 618, amplitude of the peak region 612, amplitude of the backward flow minimum 614, amplitude of the local maximum 616, etc., may change. The recommended compression rate, provided through feedback systems described herein, may be based, at least in part, on certain features of the blood flow waveforms, elapsed time period, and/or other indications of flow.

Figure 7A:
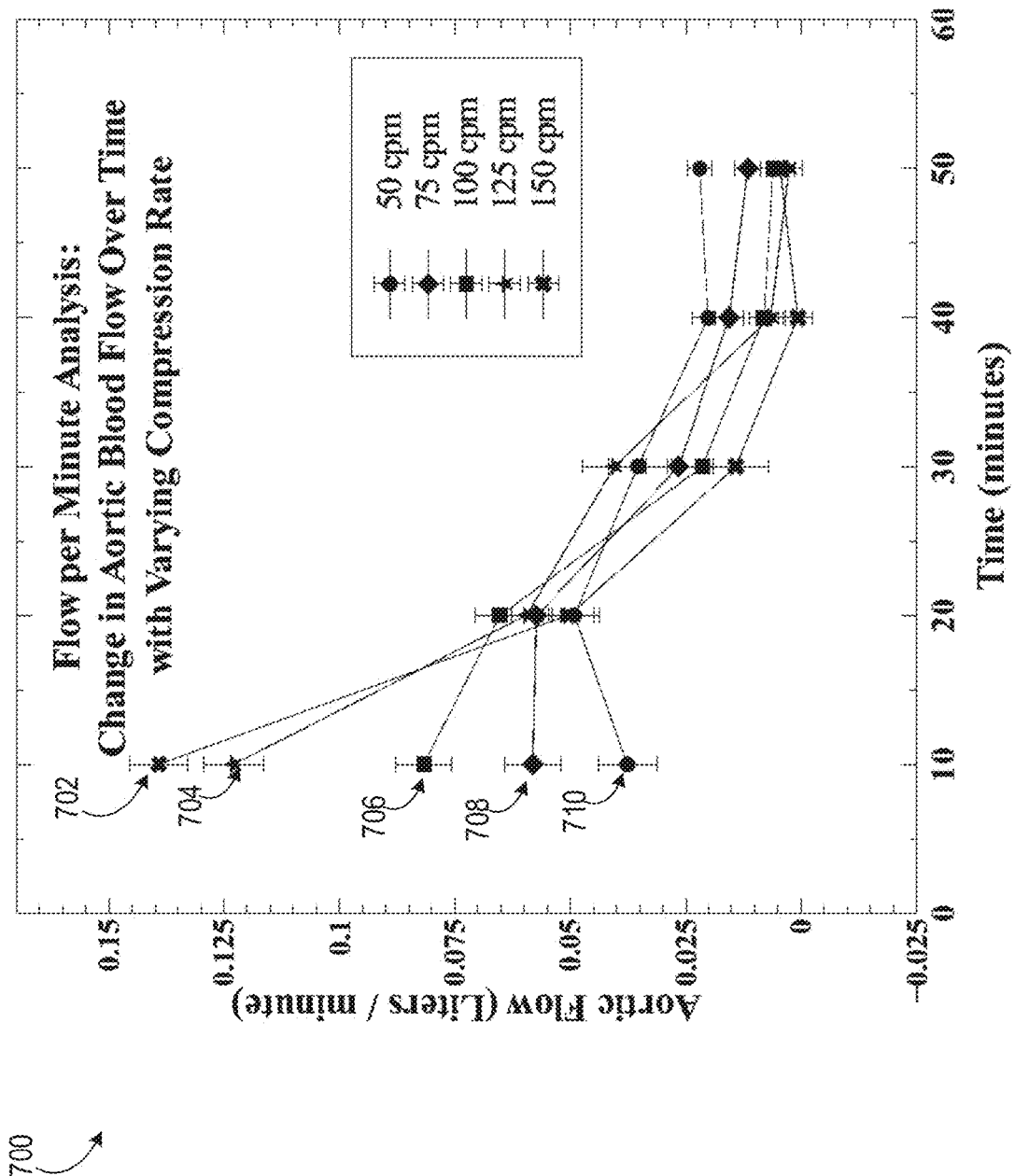
FIGS. 7A and 7B are plots of flows per minute and per compression obtained from porcine models administered according to various compression rates during resuscitation.
Figure 7B:
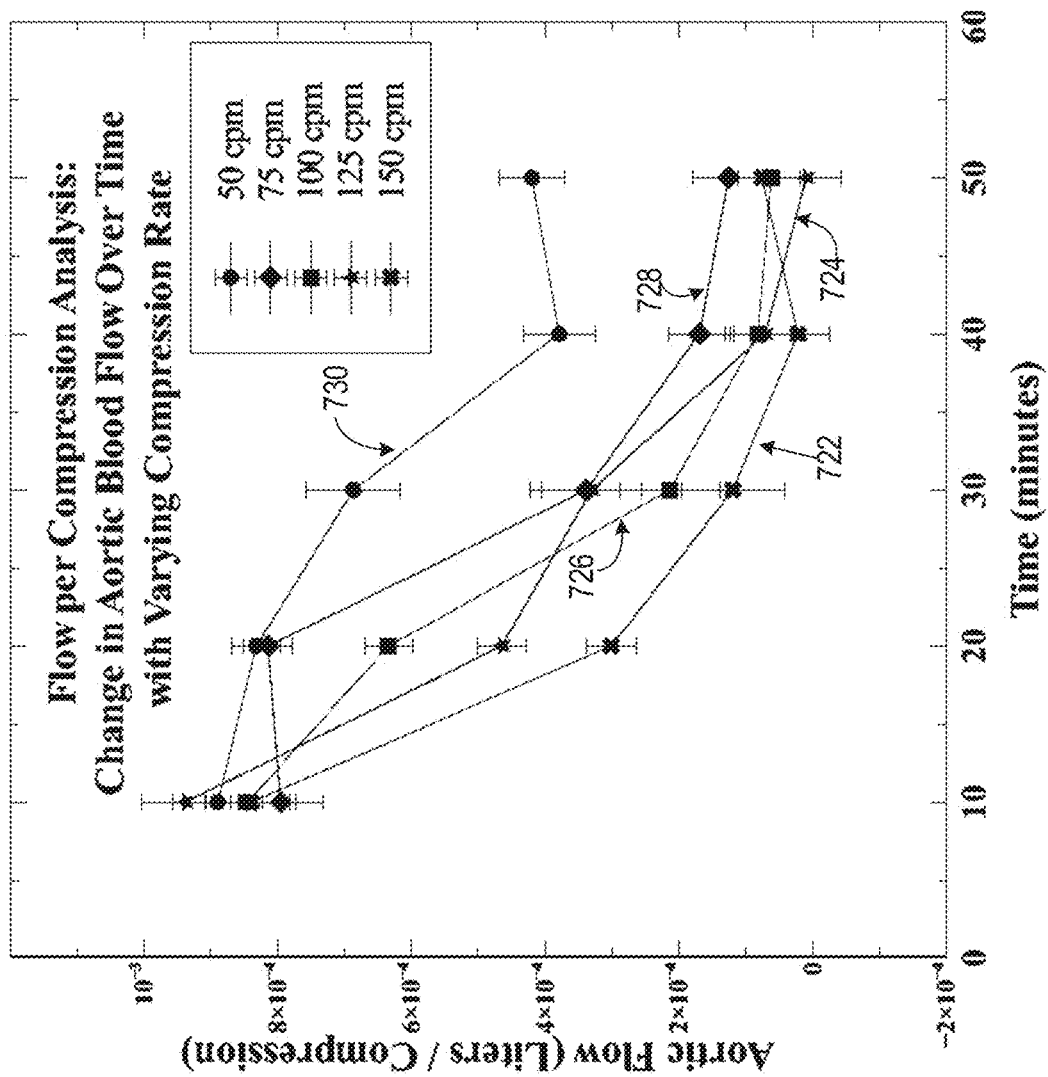

FIGS. 7A and 7B are plots of aortic flows obtained from porcine models administered various compression rates during resuscitation, as described with reference to FIG. 5. FIG. 7A illustrates a flow per minute analysis 700. The flow per minute analysis 700 includes plots of aortic flows per minute 702, 704, 706, 708, and 710 obtained from porcine models administered CPR at 150, 125, 100, 75 and 50 cpm, respectively. FIG. 7B illustrates a flow per compression analysis 720. The flow per compression analysis 720 includes plots of aortic flows per compression 722, 724, 726, 728, and 730 obtained from porcine models administered CPR at 150, 125, 100, 75 and 50 cpm, respectively.

The flow per minute analysis 700 and the flow per compression analysis 720 indicate that during the first 10 minutes of compressions, a chest compression rate of 150 cpm (illustrated by plots 702 and 722) resulted in significantly more net aortic blood flow than a rate of 50 cpm (illustrated by plots 710 and 730). This flow behavior is expected because the flow per compression analysis 720 shows that the aortic flows for all compression rates during the first 10 minutes of compressions are relatively high and similar in magnitude. Thus, more flow occurs when more compressions are given. However, during minutes 30-40 and 40-50 of continued compressions, a rate of 150 cpm (illustrated by plots 702 and 722) resulted in less net aortic blood flow than a rate of 50 cpm (illustrated by plots 710 and 730). As illustrated by the flow per compression analysis 720, the aortic flows for high compression rates (e.g., 125 cpm, 150 cpm) notably decreased as time elapsed past 30 minutes. Though, despite the decrease in flow per compression at high compression rates, the aortic flows for lower compression rates (e.g., 50 cpm, 75 cpm) stayed relatively high. Thus, while the flow for high compression rates (e.g., 150 cpm) decreased over a period of 30-50 minutes, the flow for comparatively lower compression rates (e.g., 50 cpm) remained steady. Such a finding would indicate that while higher compression rates may be beneficial to produce favorable blood flow at the beginning of chest compressions, it may be preferable to reduce the compression rate after a particular period of time to maintain a more acceptable amount of blood flow than would otherwise be produced if the compression rate were not changed.

In various porcine models, a compression rate of 150 cpm (illustrated by plots 702 and 722) was observed to empty the aortic artery of blood while a compression rate of 50 cpm (illustrated by plots 710 and 730) was observed to restore blood to the aorta. It was found that at the onset of CPR, a compression rate of 150 cpm (illustrated by plots 702 and 722) was significantly more effective at generating aortic blood flow than a compression rate of 50 cpm (illustrated by plots 710 and 730). However, as discussed above, after a particular time interval (for example, 20-40 minutes of compressions), reduced aortic flow resulted from higher compression rates (>125 cpm), suggesting that compression rates should be changed as resuscitation progresses. That is, an indication may be given to a care provider and/or chest compression system that the rate of chest compressions should be changed based on an amount of time elapsed since chest compressions have commenced. For example, this amount of time elapsed may be between approximately 5-30 minutes, between approximately 1-5 minutes, between approximately 1-10 minutes, between approximately 10-30 minutes, between approximately 20-30 minutes, between approximately 10-20 minutes, or any other suitable period of time. By way of example, for various embodiments, the change in the rate of compressions may be from a rate above 100 cpm (e.g., 100-150 cpm, 100-120 cpm, etc.) to a rate below 100 cpm (e.g., 50-100 cpm, 50-75 cpm, 75-100 cpm, etc.). In some cases, upon commencement of chest compressions, the system may check blood flow or pressure or perfusion of the patient after a preset period of time (e.g., 1 minute, 2 minutes, 3 minutes, 4 minutes, 5 minutes, 10 minutes, etc.) to determine whether the rate of compressions should be adjusted. Further, after this amount of time has elapsed, a parameter indicative of blood flow, blood pressure and/or perfusion, as measured by a sensor (e.g., perfusion: SpO2, photoplethysmographic sensor, near-infrared spectrometer) may also be used to modify the recommended rate of chest compressions.

Figure 8:
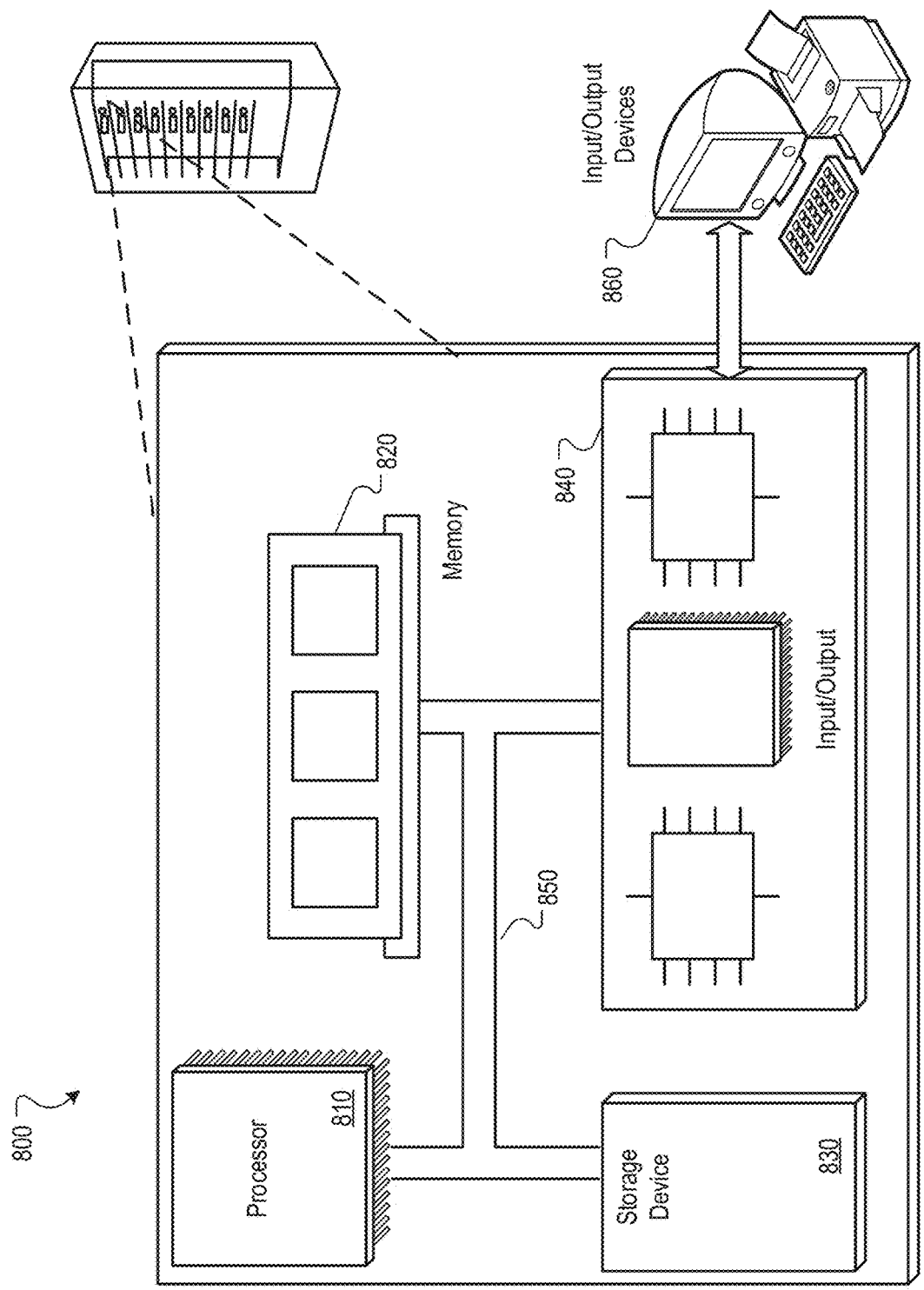
FIG. 8 is a block diagram of an example computer system.

FIG. 8 is a block diagram of an example computer system 800. For example, referring to FIG. 2, computer systems 226 could be an example of the system 800 described here, as could the monitoring device 106 as shown in FIG. 1, as could a computer system used by any of the users who interact with the monitoring device 106 as shown in FIG. 1. The system 800 includes a processor 810, a memory 820, a storage device 830, and one or more input/output interface devices 840. Each of the components 810, 820, 830, and 840 can be interconnected, for example, using a system bus 850.

The processor 810 is capable of processing instructions for execution within the system 800. The term "execution" as used here refers to a technique in which program code causes a processor to carry out one or more processor instructions. In some implementations, the processor 810 is a single-threaded processor. In some implementations, the processor 810 is a multi-threaded processor. In some implementations, the processor 810 is a quantum computer. The processor 810 is capable of processing instructions stored in the memory 820 or on the storage device 830. The processor 810 can execute operations such as assistance of CPR treatment.

The memory 820 stores information within the system 800. In some implementations, the memory 820 is a computer-readable medium. In some implementations, the memory 820 is a volatile memory unit. In some implementations, the memory 820 is a non-volatile memory unit.

The storage device 830 is capable of providing mass storage for the system 800. In some implementations, the storage device 830 is a non-transitory computer-readable medium. In various different implementations, the storage device 830 can include, for example, a hard disk device, an optical disk device, a solid-date drive, a flash drive, magnetic tape, or some other large capacity storage device. In some implementations, the storage device 830 can be a cloud storage device (e.g., a logical storage device including one or more physical storage devices distributed on a network and accessed using a network), such as the network 206 shown in FIG. 2. In some examples, the storage device can store long-term data, such as data described in this application as stored on a patient information system 224 as shown in FIG. 2. The input/output interface devices 840 provide input/output operations for the system 800. In some implementations, the input/output interface devices 840 can include one or more of a network interface devices (e.g., an Ethernet interface), a serial communication device (e.g., an RS-232 interface), and/or a wireless interface device (e.g., an 802.11 interface), a 3G wireless modem, a 4G wireless modem, etc. A network interface device allows the system 800 to communicate, for example, transmit and receive data such as data described in this application as being communicated by way of a network 206, as shown in FIG. 2. In some implementations, the input/output device can include driver devices configured to receive input data and send output data to other input/output devices (e.g., keyboard, printer and display devices 860). In some implementations, mobile computing devices, mobile communication devices, and other devices can be used.

Computer program modules can be realized by instructions that upon execution cause one or more processing devices to carry out the processes and functions described above, for example, assistance of CPR. Such instructions can include, for example, interpreted instructions such as script instructions, or executable code, or other instructions stored in a computer readable medium. In general, a module can include software, hardware, or a combination of both.

A server 232 as shown in FIG. 2 can be distributively implemented over a network, such as a server farm, or a set of widely distributed servers or can be implemented in a single virtual device that includes multiple distributed devices that operate in coordination with one another. For example, one of the devices can control the other devices, or the devices can operate under a set of coordinated rules or protocols, or the devices can be coordinated in another fashion. The coordinated operation of the multiple distributed devices presents the appearance of operating as a single device.

In some examples, the system 800 is contained within a single integrated circuit package. A system 800 of this kind, in which both a processor 810 and one or more other components are contained within a single integrated circuit package and/or fabricated as a single integrated circuit, is sometimes called a microcontroller. In some implementations, the integrated circuit package includes pins that correspond to input/output ports that can be used to communicate signals to and from one or more of the input/output interface devices 840.

Although an example processing system has been described in FIG. 2, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, (e.g., one or more modules of computer program instructions encoded on a tangible program carrier, for example a computer-readable medium, for execution by, or to control the operation of, a processing system). The computer readable medium can be a machine readable storage device, a machine readable storage substrate, a memory device, or a combination of one or more of them.

The term "system" can encompass all apparatus, devices, and machines for processing data, including by way of example a programmable processor, a computer, or multiple processors or computers. A processing system can include, in addition to hardware, code that creates an execution environment for the computer program in question (e.g., code that constitutes processor firmware), a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices (e.g., EPROM, EEPROM, and flash memory devices); magnetic disks (e.g., internal hard disks or removable disks or magnetic tapes); magneto optical disks; and CD-ROM, DVD-ROM, and Blu-Ray disks. The processor and the memory can be supplemented by, or incorporated in, special purpose logic circuitry. Sometimes a server (e.g., server 232 as shown in FIG. 2) is a general purpose computer, and sometimes it is a custom-tailored special purpose electronic device, and sometimes it is a combination of these things. Implementations can include a back end component (e.g., a data server), or a middleware component (e.g., an application server), or a front end component (e.g., a client computer having a graphical user interface) or a Web browser, through which a user can interact with an implementation of the subject matter described is this specification, or any combination of one or more such back end, middleware, or front end components. The components of the system can be interconnected by any form or medium of digital data communication (e.g., a communication network such as the network 206 shown in FIG. 2). Examples of communication networks include a local area network ("LAN") and a wide area network ("WAN"), e.g., the Internet.

Many other implementations other than those described can be employed, and can be encompassed by the following claims.

What is claimed is:

1. A system for assisting with a chest compression treatment being administered to a patient, the system comprising:
   a sensor configured to be attached to a patient's skin for generating signals indicative of blood flow resulting from administered chest compressions to the patient; and
   one or more processors configured for:
      detecting that chest compression administration has been initiated;
      receiving the signals from the sensor indicative of blood flow from the administered chest compressions,
      determining, based on the received signals, a blood flow parameter resulting from the administered chest compressions,
      determining, based on the blood flow parameter, that the blood flow resulting from the administered chest compressions has decreased over a predetermined time interval from the detection that the chest compression administration had been initiated,
      determining, based on the determined decrease of the blood flow resulting from the administered chest compressions, that a rate of chest compressions should be changed to a slower rate, and
      providing an output comprising an indication that the rate of chest compressions should be changed to the slower rate.

2. The system of claim 1, wherein the parameter comprises at least one of a blood flow, blood flow volume, blood flow velocity, a pulse wave velocity and a blood pressure.

3. The system of claim 2, wherein determining at least one of a blood flow, blood flow volume, blood flow velocity, a pulse wave velocity and a blood pressure comprises obtaining at least one of a blood flow waveform and a blood pressure waveform.

4. The system of claim 3, wherein determining, based on the parameter, whether the rate of chest compressions administered in the chest compression treatment should be changed comprises processing the parameter to identify a portion of at least one of the blood flow waveform and the blood pressure waveform.

5. The system of claim 4, wherein determining that the rate of chest compressions administered in the chest compression treatment should be changed comprises identifying a change of the portion of at least one of the blood flow waveform and the blood pressure waveform.

6. The system of claim 4, wherein at least one of the blood flow waveform and the blood pressure waveform corresponds to at least one of an inferior vena cava, a carotid artery, a jugular vein, a brachial artery, a femoral artery, and an abdominal aorta.

7. The system of claim 1, wherein the rate of chest compressions is gradually changed during a plurality of time intervals based on an amount of time elapsed since chest compressions are commenced.

8. The system of claim 7, wherein the amount of time elapsed is between 5 minutes and 30 minutes.

9. The system of claim 1, wherein the indication that the rate of chest compressions should be changed comprises the indication to decrease the rate of chest compressions to a revised rate.

10. The system of claim 9, wherein the revised rate comprises less than 75 compressions per minute.

11. The system of claim 10, comprising a metronome to convey the revised rate.

12. The system of claim 9, wherein the revised rate comprises less than 100 compressions per minute.

13. The system of claim 9, wherein the revised rate comprises 50 compressions per minute.

14. The system of claim 1, comprising a user interface configured to provide the indication using at least one of audible prompts and visual prompts.

15. The system of claim 14, wherein the user interface is configured to operate in a first mode for displaying a first set of information and a second mode for displaying a second set of information, different from the first set of information.

16. The system of claim 14, wherein the audible prompts comprise audible instructions and the visual prompts comprise visual instructions.

17. The system of claim 14, wherein the user interface is configured to provide the indication by communicating with an external device.

18. The system of claim 1, comprising a motion sensor configured to measure rate of chest compressions exerted on the patient.

19. The system of claim 18, wherein the indication comprises a prompt to change a compression rate based on processing data from the motion sensor.

20. The system of claim 1, wherein determining the parameter indicative of the blood flow comprises:
determining a test parameter trajectory based on the signals; and
comparing the test parameter trajectory to a control parameter trajectory to determine a deviation of the test parameter trajectory from the control parameter trajectory over a plurality of cardiac cycles.

21. The system of claim 20, wherein comparing the test parameter trajectory to the control parameter trajectory comprises determining a trend of the deviation of the test parameter trajectory.

22. A system for assisting with a chest compression treatment being administered to a patient, the system comprising:
a sensor configured to be attached to a patient body surface for generating signals indicative of a cardiac output resulting from administered chest compressions to the patient;
a timer configured to determine an amount of time elapsed since chest compressions are commenced; and
one or more processors configured for:
detecting that chest compression administration has been initiated;
receiving, from the sensor, the signals indicative of blood flow from the administered chest compressions,
determining, based on the received signals, a cardiac output parameter resulting from the administered chest compressions,
determining, based on the cardiac output parameter, that the cardiac output resulting from the administered chest compressions has decreased over a predetermined time interval from the detection that the chest compression administration had been initiated,
determining, based on the determined decrease of the cardiac output resulting from the administered chest compressions, that a rate of chest compressions administered in the chest compression treatment should be changed to a slower rate; and
providing an indication to a user that the rate of chest compressions should be changed to the slower rate.

23. The system of claim 22, wherein the slower rate comprises less than 100 compressions per minute.

24. The system of claim 22, wherein the slower rate comprises less than 75 compressions per minute.

25. The system of claim 22, wherein the slower rate comprises 50 compressions per minute.

26. The system of claim 22, further comprising a sensor configured to measure a parameter indicative of at least one of blood flow, blood pressure and perfusion.

27. The system of claim 26, wherein the indication that the rate of chest compressions should be changed is based on the parameter indicative of at least one of blood flow, blood pressure and perfusion.

28. The system of claim 22, wherein determining that the cardiac output has decreased comprises comparing the amount of time elapsed to a threshold.

29. The system of claim 28, wherein the threshold is between 15 and 25 minutes.

30. The system of claim 22, comprising a metronome to convey the slower rate.

31. The system of claim 30, wherein the indication that the rate of chest compressions should be changed comprises an indication to decrease the rate of chest compressions to at least one predetermined rate.

32. A system for assisting with a chest compression treatment being administered to a patient, the system comprising:
a first sensor configured to be attached to a patient body surface for measuring signals indicative of blood flow resulting from administered chest compressions to the patient;
a metronome to guide a user in applying chest compressions at a first rate;
a motion sensor configured to measure a rate of chest compressions exerted on the patient;
one or more processors configured for:
detecting that chest compression administration has been initiated;
receiving the signals from the first sensor and the motion sensor indicative of blood flow from the administered chest compressions,
determining, based on the received signals, a blood flow parameter resulting from the administered chest compressions,
determining, based on the blood flow parameter, that the blood flow resulting from the administered chest compressions has decreased, over a predetermined time interval from the detection that the chest compression administration had been initiated, determining, based on the determined decrease of blood flow resulting from the administered chest compressions, that a rate of chest compressions should be changed to a second rate that is slower than the rate of chest compressions exerted by on the patient; and a user interface configured to provide feedback indicating that the rate of chest compressions is to be changed, and provide the second rate to guide the user in applying chest compressions.

33. A system for assisting with a chest compression treatment being administered to a patient, the system comprising:

a timer configured to determine an amount of time elapsed since chest compressions are commenced;

a parameter sensor configured to determine a blood flow metric;

a mechanical chest compression device;

a mechanical chest compression device controller; and one or more processors configured for:

instructing the mechanical chest compression device controller to provide chest compressions at a first rate to initiate chest compression administration, receiving, from the parameter sensor, the blood flow metric indicative of blood flow from the administered chest compressions, determining, based on the received blood flow metric, blood flow parameter resulting from the administered chest compressions;

determining, based on the blood flow parameter that the blood flow resulting from the administered chest compressions has decreased over a predetermined time interval from when the chest compression administration had been initiated, determining, based on the determined decrease of blood flow resulting from the administered chest compressions, that a rate of chest compressions administered in the chest compression treatment should be changed to a second rate that is slower than the rate of chest compressions exerted on the patient, and providing a second rate of chest compressions based on the time elapsed.

34. A method for assisting with a chest compression treatment administered to a patient, the method comprising:

detecting, by one or more processors, that chest compression administration has beers initiated;

receiving, by the one or more processors and from a sensor configured to be attached to a patient's skin, signals measuring a waveform indicative of at least one of a blood flow, a pulse wave velocity and a blood pressure of the patient from the administered chest compressions;

determining, by the one or more processors, based on the received signals, a waveform parameter resulting from the administered chest compressions, determining, by the one or more processors and based on the waveform parameter, the blood flow resulting from the administered chest compressions has decreased over a predetermined time interval from the detection that the chest compression administration had been initiated, determining, by the one or more processors, based on the determined decrease of the blood flow or of a cardiac output resulting from the administered chest compressions, that a rate of chest compressions administered in the chest compression treatment should be changed to a slower rate; and providing, by the one or more processors, an indication that the rate of chest compressions should be changed to the slower rate.

35. The method of claim 34, comprising processing, by one or more processors, the waveform to identify a variation of a feature of the waveform.

36. The method of claim 35, wherein processing comprises:

detecting a shape of the feature within the waveform; and detecting a change of the shape of the feature of the waveform.

37. The method of claim 36, wherein the waveform corresponds to at least one of an inferior vena cava, a carotid artery, a brachial artery, a femoral artery, and an abdominal aorta.

* * * * *